United States Patent
Santiago

(10) Patent No.: US 10,864,090 B2
(45) Date of Patent: Dec. 15, 2020

(54) SPINAL IMPLANT SYSTEM AND METHODS OF USE

(71) Applicant: Warsaw Orthopedic, Inc., Warsaw, IN (US)

(72) Inventor: Dawin Rodriguez Santiago, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 16/391,971

(22) Filed: Apr. 23, 2019

(65) Prior Publication Data

US 2020/0337858 A1 Oct. 29, 2020

(51) Int. Cl.
*A61B 17/70* (2006.01)
*A61F 2/46* (2006.01)
*A61F 2/44* (2006.01)
*A61F 2/28* (2006.01)

(52) U.S. Cl.
CPC ............ *A61F 2/4611* (2013.01); *A61F 2/442* (2013.01); *A61F 2/4465* (2013.01); *A61F 2002/2835* (2013.01); *A61F 2310/00023* (2013.01)

(58) Field of Classification Search
CPC ............ A61B 17/8685; A61B 17/7032; A61B 17/7037
USPC .................................................. 606/268, 269
See application file for complete search history.

(56) References Cited

U.S. PATENT DOCUMENTS

| | | | |
|---|---|---|---|
| 2012/0109218 A1* | 5/2012 | Farris ................. | A61B 17/8685 606/305 |
| 2014/0257411 A1* | 9/2014 | Rezach .............. | A61B 17/7037 606/305 |
| 2016/0262801 A1* | 9/2016 | Rezach .............. | A61B 17/7038 |
| 2016/0317206 A1* | 11/2016 | Rezach .............. | A61B 17/7037 |
| 2017/0281241 A1* | 10/2017 | Jackson ............. | A61B 17/7037 |
| 2018/0193062 A1* | 7/2018 | May ................... | A61B 17/7035 |
| 2018/0193063 A1* | 7/2018 | May ..................... | A61B 17/70 |

* cited by examiner

*Primary Examiner* — Jan Christopher L Merene
(74) *Attorney, Agent, or Firm* — Sorell, Lenna & Schmidt, LLP

(57) ABSTRACT

A bone fastener includes a receiver defining an implant cavity and having an inner surface defining a slot. A band is disposable within the slot. A spacer disposable within the slot. A crown is rotatable relative to the receiver to translate the spacer relative to the inner surface such that the spacer orients the band in a capture orientation with the shaft. A screw shaft connectable with the receiver by the band and configured to penetrate tissue. Implants, systems, instruments and methods are disclosed.

21 Claims, 13 Drawing Sheets

SPINAL IMPLANT SYSTEM AND METHODS OF USE

TECHNICAL FIELD

The present disclosure generally relates to medical devices for the treatment of spinal disorders, and more particularly to a surgical implant system including a bone fastener and a related method.

BACKGROUND

Spinal pathologies and disorders such as scoliosis, kyphosis, and other curvature abnormalities, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods and bone fasteners are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a bone fastener is provided. The bone fastener includes a receiver defining an implant cavity and having an inner surface defining a slot. A band is disposable within the slot. A spacer disposable within the slot. A crown is rotatable relative to the receiver to translate the spacer relative to the inner surface such that the spacer orients the band in a capture orientation with the shaft. A screw shaft connectable with the receiver by the band and configured to penetrate tissue. In some embodiments, implants, systems, instruments and methods are disclosed.

In one embodiment, the bone fastener includes an implant receiver having a slot. A spacer is disposed with the slot. An expanded ring is disposable within the slot. A threaded shaft includes a head. A crown is disposed with the receiver and is rotatable relative to the receiver to axially translate a spacer relative to the inner surface such that a ramp surface of the spacer engages the ring in a capture orientation with the head.

In one embodiment, a spinal implant system is provided. The spinal implant system includes a bone fastener having an implant receiver and a shaft configured to penetrate tissue. The implant receiver has a band and a crown being rotatable relative to the implant receiver to translate a spacer relative to the implant receiver such that the spacer orients the band in a capture orientation with the shaft. A spinal rod is disposable with the implant receiver. A coupling member is engageable with the implant receiver and the spinal rod such that the spacer and the band are disposed in a lock configuration.

BRIEF DESCRIPTION OF THE DRAWINGS

The present disclosure will become more readily apparent from the specific description accompanied by the following drawings, in which.

DETAILED DESCRIPTION

Figure 1:
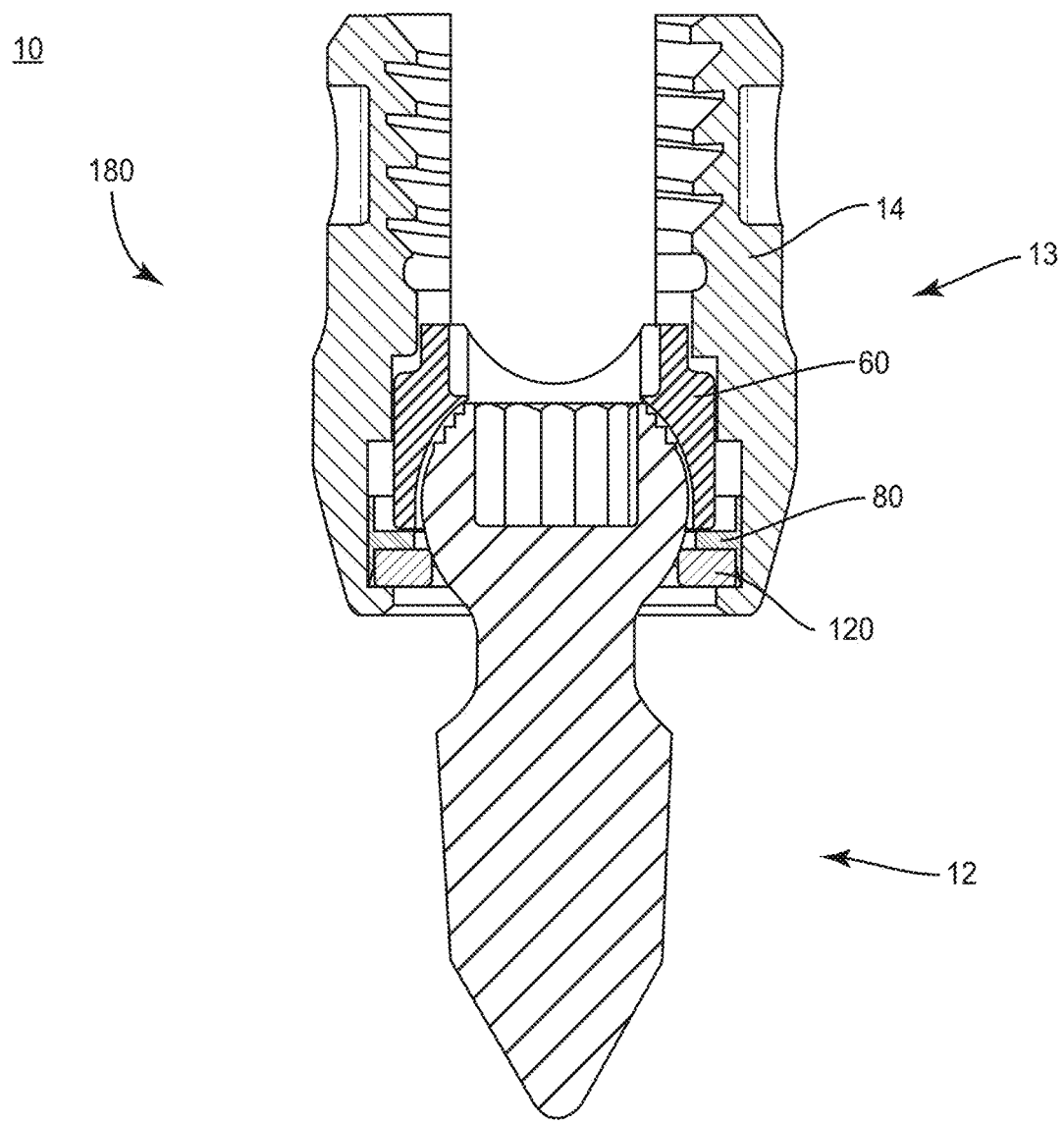
FIG. 1 is a side cross section view of components of one embodiment of a spinal implant system in accordance with the principles of the present disclosure.

The exemplary embodiments of a surgical system and related methods of use disclosed are discussed in terms of medical devices for the treatment of musculoskeletal disorders and more particularly, in terms of a spinal implant system including a bone fastener. In one embodiment, the present spinal implant system includes an implant comprising a bone fastener, such as, for example, a pedicle bone screw.

In some embodiments, the present spinal implant system comprises a modular bone screw including one or more components, for example, a screw shaft and a head configured for assembly in-situ, during an operating room procedure, on a back table, and/or at a manufacturing facility. In some embodiments, the bone screw includes a spacer configured for disposal between a position, for example, which allows for expansion of a snap ring and a position, for example, which resists and/or prevents the snap ring from expanding. In some embodiments, the spacer engages an outside diameter of the snap ring to resist and/or prevent expansion. In some embodiments, the spacer is disposed in an expandable position such that the spacer is disengaged from the snap ring. In some embodiments, assembly of the bone screw includes engaging a rod and a setscrew with the bone screw. In some embodiments, rotation of the setscrew causes the spacer to engage the outside diameter of the snap ring. In some embodiments, the spacer is manipulated between the positions by a member, such as, for example, a crown. In some embodiments, the crown includes a cam feature configured to engage a head portion of the bone screw.

In some embodiments, the bone screw is configured to be disassembled, for example, the crown is configured for manipulation, as described herein, from a first position to a second position and then back to the first position. In some embodiments, the bone screw is configured for use without a secondary expansion chamber for the snap ring. In some embodiments, the bone screw includes an active engagement member, such as, for example, a quarter turn cam interface that indicates the assembly is fully engaged to a user.

In some embodiments, the spinal implant system comprises a modular system that includes a bone screw having a bone screw shaft, a ring, a spacer, a crown and a receiver. In some embodiments, the bone screw is selectively coupled in a non-instrumented assembly and/or manual assembly method that includes the step of disposing the crown with the head. In some embodiments, the method includes the step of assembling a head sub-assembly. In some embodiments, the method includes the step of disposing the spacer with the head. In some embodiments, the method includes the step of fully seating the spacer with the head. In some embodiments, the method includes the step of disposing the ring with the head. In some embodiments, the method includes the step of connecting the bone screw shaft with the head sub-assembly. In some embodiments, the step of connecting the bone screw shaft with the head sub-assembly includes seating a proximal end of the bone screw shaft with the crown. In some embodiments, the step of connecting the bone screw shaft with the head sub-assembly includes rotating the crown to a selected position, as described herein. In some embodiments, the step of connecting the bone screw shaft with the head sub-assembly includes rotating the crown to a lock position. In some embodiments, the step of connecting the bone screw shaft with the head sub-assembly includes rotating the crown through a selected angular range. In some embodiments, the step of connecting the bone screw shaft with the head sub-assembly includes rotating the crown to a selected angle, for example, 90 degrees.

In some embodiments, the spinal implant system comprises a modular system that includes a bone screw having an array of members, such as, for example, bone screw shafts that can be selectively coupled to members, such as, for example, receivers. In some embodiments, the spinal implant system comprises a selectively coupled bone screw that can be assembled on a surgical table or in-situ. In some embodiments, the bone screw is selectively coupled with a non-instrumented assembly and/or manual assembly. In some embodiments, the non-instrumented assembly comprises manually engaging a screw shaft with a head/receiver of the bone screw. In some embodiments, the non-instrumented assembly comprises manually engaging the screw shaft in a pop-on engagement with the head/receiver of the bone screw. In some embodiments, a force required to manually engage a screw shaft with a head/receiver of the bone screw in a non-instrumented assembly is in a range of 2 to 50 N. In some embodiments, a force required to manually engage a screw shaft with a head/receiver of the bone screw in a non-instrumented assembly is in a range of 5 to 10 N. In some embodiments, this configuration provides manually engageable components of a bone screw that are assembled without instrumentation, and subsequent to assembly, the assembled components have a selected pull-out strength and/or can be pulled apart, removed and/or separated with a minimum required force.

In some embodiments, the bone screw is configured for assembly without the use of an instrument, such as, for example, a practitioner, surgeon and/or medical staff utilizes their hands for assembly. In some embodiments, the system requires minimal force to attach an implant receiver and a screw shaft assembly in-situ thereby reducing a pre-load on the vertebrae, such as, for, example, the pedicle. In some embodiments, the bone screw includes an expandable ring.

In some embodiments, the present disclosure may be utilized with various medical procedures. In some embodiments, the present disclosure may be utilized in various industries, for example, construction.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-15, there are illustrated components of a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant, such as, for example, a bone fastener 180. Bone fastener 180 comprises a screw shaft 12 and a head assembly 13, as shown in FIG. 1. Head assembly 13 includes a receiver 14 and a crown 60 that is configured for rotation relative to receiver 14 to orient a band, such, as, for example, a ring 120 disposed with receiver 14 in a contracted, or capture, orientation, to attach receiver 14 with screw shaft 12. The orientation is referred to as a contracted, or capture, orientation because head assembly 13 is attached with screw shaft 12 by ring 120 in the contracted, or capture, orientation.

In some embodiments or implementations, screw shaft 12 and head assembly 13 are assembled in situ, during an operating room procedure, such as on a back table of the room, and/or at a manufacturing facility, as described herein.

Figure 2:
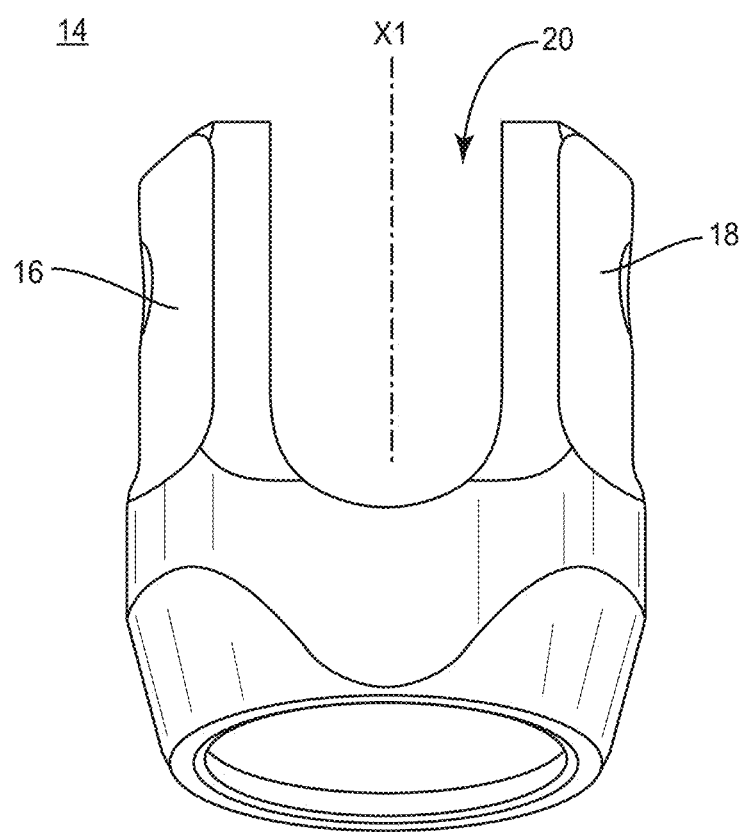
FIG. 2 is a perspective view of a component of the system shown in FIG. 1.

With reference also to FIG. 2, receiver 14 extends along and defines a central axis X1. Receiver 14 includes a pair of spaced-apart arms 16, 18 that define an implant cavity 20 therebetween configured for disposal of a component, such as, for example, a spinal rod 200 (FIG. 15) of a spinal construct, as described herein. Arms 16, 18 each extend parallel to axis X1. In some embodiments, arm 16 and/or arm 18 may be disposed at alternate orientations, relative to axis X1, such as, for example, transverse, perpendicular and/or other angular orientations such as acute or obtuse, coaxial and/or may be offset or staggered, relative to axis X1. Arms 16, 18 each include an outer surface extending between a pair of side surfaces. The outer surfaces may each be fully or partially arcuate or rounded.

Arms 16, 18 each include an outer surface extending between a pair of side surfaces. The outer surfaces may each be fully or partially arcuate or rounded. In various embodiments, at least one of the outer surfaces and the side surfaces of arms 16, 18 have therein at least one recess or cavity configured to receive an insertion tool, compression instrument and/or instruments for inserting and, possibly also tensioning, bone fastener 180.

In some embodiments (not shown in detail), arms 16, 18 are connected to each other at proximal and distal ends thereof such that receiver 14 defines a closed spinal rod slot.

In some embodiments, a spinal rod may be monolithically formed with receiver 14 or pre-assembled with receiver 14.

Cavity 20 is, in various embodiments, substantially U-shaped. In some embodiments, all or only a portion of cavity 20 has alternate cross-section configurations, such as, for example, closed, V-shaped, W-shaped, oval, oblong triangular, square, polygonal, irregular, uniform, non-uniform, offset, staggered, and/or tapered.

Figure 3:
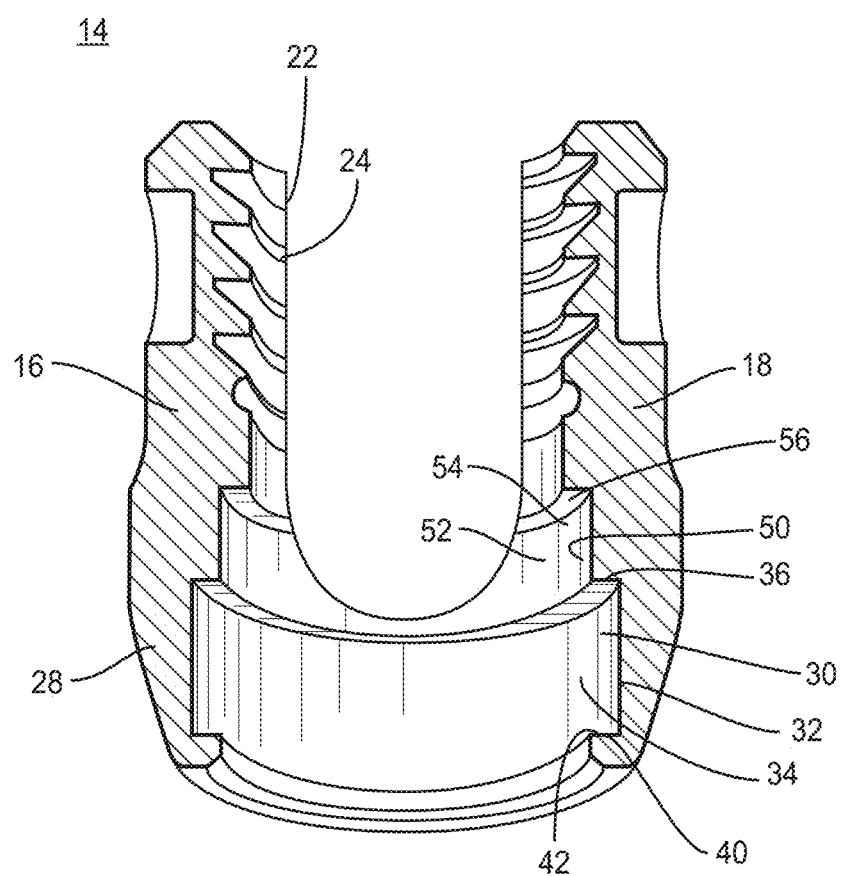
FIG. 3 is a cross section view of the component shown in FIG. 2.

Receiver 14 includes inner surfaces 22, as called out in FIG. 3. The inner surfaces 22 may each be fully or partially arcuate or rounded. A portion of surface 22 includes a thread form 24 located adjacent arm 16 and located adjacent arm 18. Thread form 24 is configured for engagement with a coupling member, such as, for example, a setscrew 202, to retain spinal rod 200 within cavity 20. In some embodiments, surface 22 may be disposed with the coupling member in alternative fixation configurations, besides thread fit, such as, for example, friction fit, pressure fit, locking protrusion/recess, locking keyway and/or adhesive. In some embodiments, all or only a portion of surface 22 has any of one or more of numerous surface configurations to enhance engagement with spinal rod 200 and/or setscrew 202, such as, for example, rough, arcuate, undulating, mesh, porous, semi-porous, dimpled and/or textured. In some embodiments, receiver 14 includes any of one or more of various alternative configurations, such as, for example, closed, open and/or side access.

Receiver 14 includes a portion 28, as shown in FIG. 2. Portion 28 includes a wall 32 having a surface 30. Surface 30 may have a continuous and non-interrupted configuration. Wall 32 defines a cavity, such as, for example, a slot 34. Slot 34 is configured for selective translation of a spacer 80, as described herein. Slot 34 includes a proximal portion 36 and a distal portion 40. Distal portion 40 includes a stop surface 42 at a distalmost portion of slot 34. Surface 42 provides a distal limit for translation of ring 120. In some embodiments, all or only a portion of surface 30 has any of one or more of various surface configurations to enhance engagement with spacer 80, such as, for example, rough, arcuate, undulating, mesh, porous, semi-porous, dimpled and/or textured.

Receiver 14 further includes a surface 50. Surface 50 defines a cavity, such as, for example, a slot 52. Slot 52 is configured for disposal and translation of crown 60, as described herein. Slot 52 includes a proximal portion 54 having a ridge 56. Ridge 56 provides a proximal limit for translation of crown 60. In various embodiments, all or only a portion of surface 50 has any one or more of numerous alternative surface configurations to enhance engagement with crown 60, such as, for example, rough, arcuate, undulating, mesh, porous, semi-porous, dimpled and/or textured.

Figure 4:
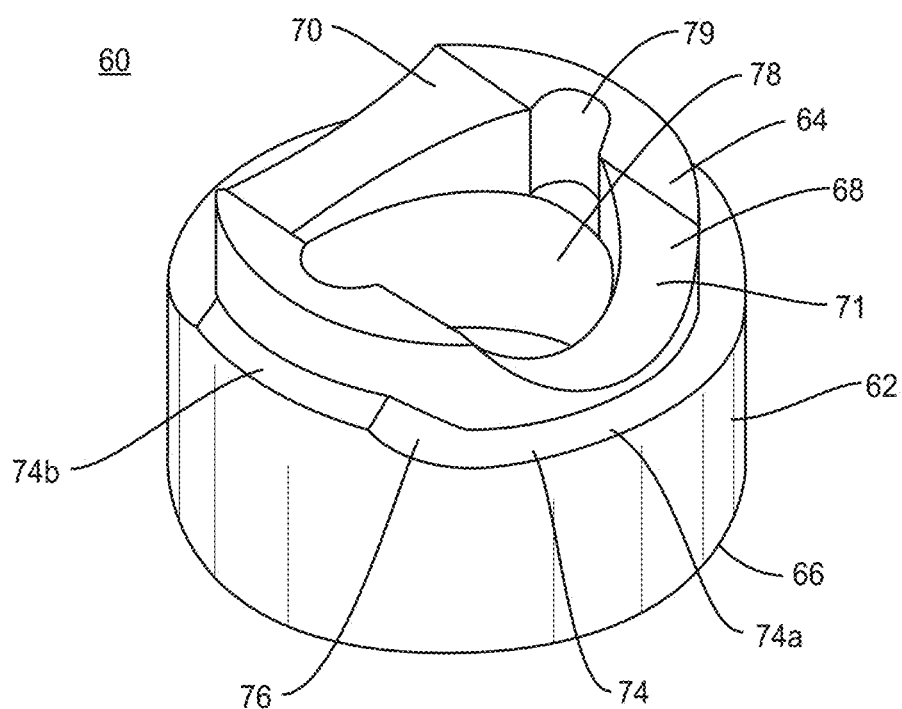
FIG. 4 is a perspective view of a second component of the system shown in FIG. 1.

Crown 60 is configured for disposal within slot 52. Crown 60 is configured for rotation relative to receiver 14 to orient ring 120 disposed with receiver 14 in a contracted, or capture, orientation, to fix receiver 14 with screw shaft 12. Crown 60 includes a wall 62 having an end surface 64 and an end surface 66, as shown in FIG. 4. Portion 68 includes an outer surface 70. The outer surface 70 defines a curved portion 71 of crown 60. The curved portion 71 is configured to receive spinal rod 200.

In various embodiments, crown 60 also includes a tool-engaging portion 79 configured to engage a surgical tool or instrument to actuate rotation of crown 60. In some embodiments, portion 79 includes one or more (e.g., an opposing pair, as shown in FIG. 4) cutouts shaped in profile or cross section as fully or partially arcuate, rectangular, polygonal, hexalobe, oval, or irregular, as just a few examples.

Figure 14:
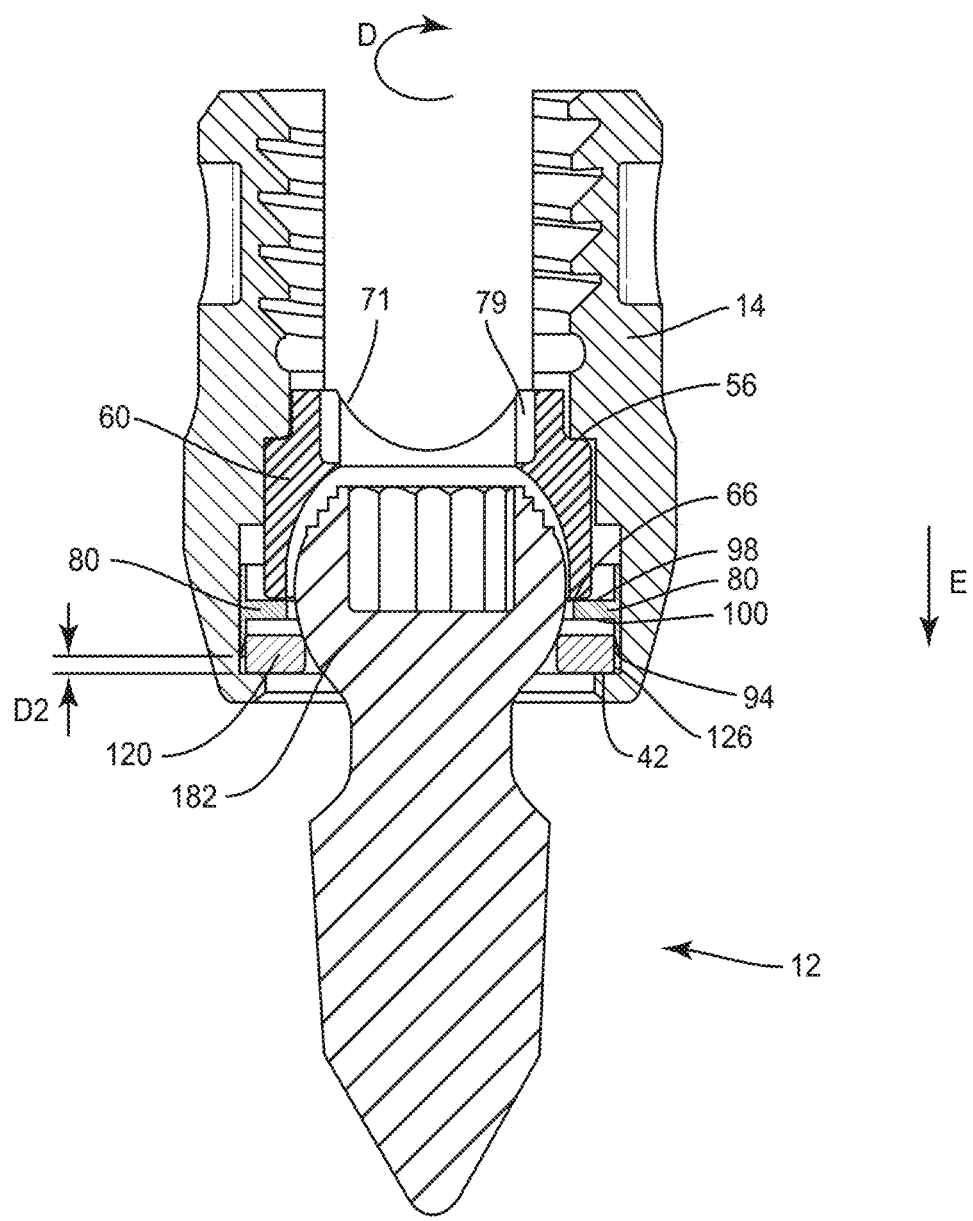
FIG. 14 is a side cross section view of the components of the system in a seventh position.
Figure 15:
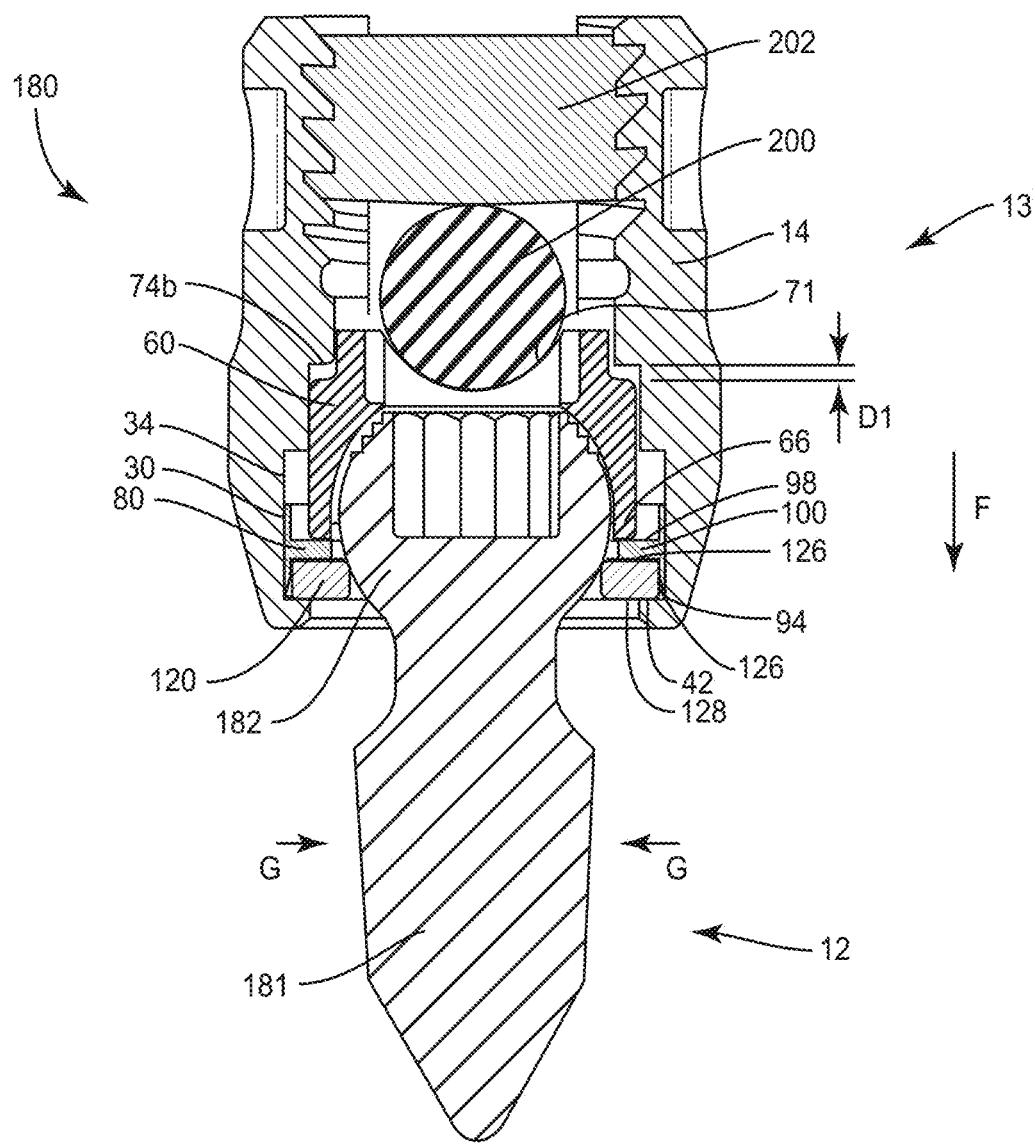
FIG. 15 is a side cross section view of the components of the system in a final position.

Crown 60 includes a circumferential ridge 74. The ridge 74 is in various embodiments configured to form at least one cam feature. Ridge 74 may be configured for engagement with ridge 56 of receiver 14 to convert rotational movement of crown 60 into linear movement of crown 60, along axis X1, to drive spacer 80 into the capture orientation, as described herein. In some embodiments, for example, ridge 74 includes a portion 74a, a portion 74b, and a transition surface, such as, for example, a ramp 76. Ramp 76 is disposed between portion 74a and portion 74b to convert the rotational movement to linear movement. In various embodiments, portion 74b is raised relative to portion 74a a distance D1, which is generally equal to a distance D2 that spacer 80 travels in being translated into engagement with stop surface 42 (FIGS. 14 and 15). Ramp 76 is inclined between portion 74a and portion 74b to facilitate translation of crown 60 and translation of spacer 80 distance D2 relative to ring 120, as described herein.

The ramp is configured as desired by the designer to balance various performance characteristics. The desired angle may balance, for instance, the change in crown height achievable by use of the ramp against ease, or facility, for the user in turning the crown to achieve that height. A steeper ramp would allow for more height change, but could be harder to accomplish manually. Steeper ramp angles could also conceivable cause some sticking, requiring the user to turn again or harder to get past that point.

While one ramp is clearly visible in FIG. 4, there are two opposing ramps in that embodiment. In various embodiments, the crown 60 can include other numbers of ramps, such as two sets of opposing ramps, three equally spaced ramps, or even a single ramp. In some cases, one or more ramps are two-sided, allowing a user to accomplish the height change whether turning the crown in a first direction (e.g., clockwise) or an opposite second direction.

Figure 8:
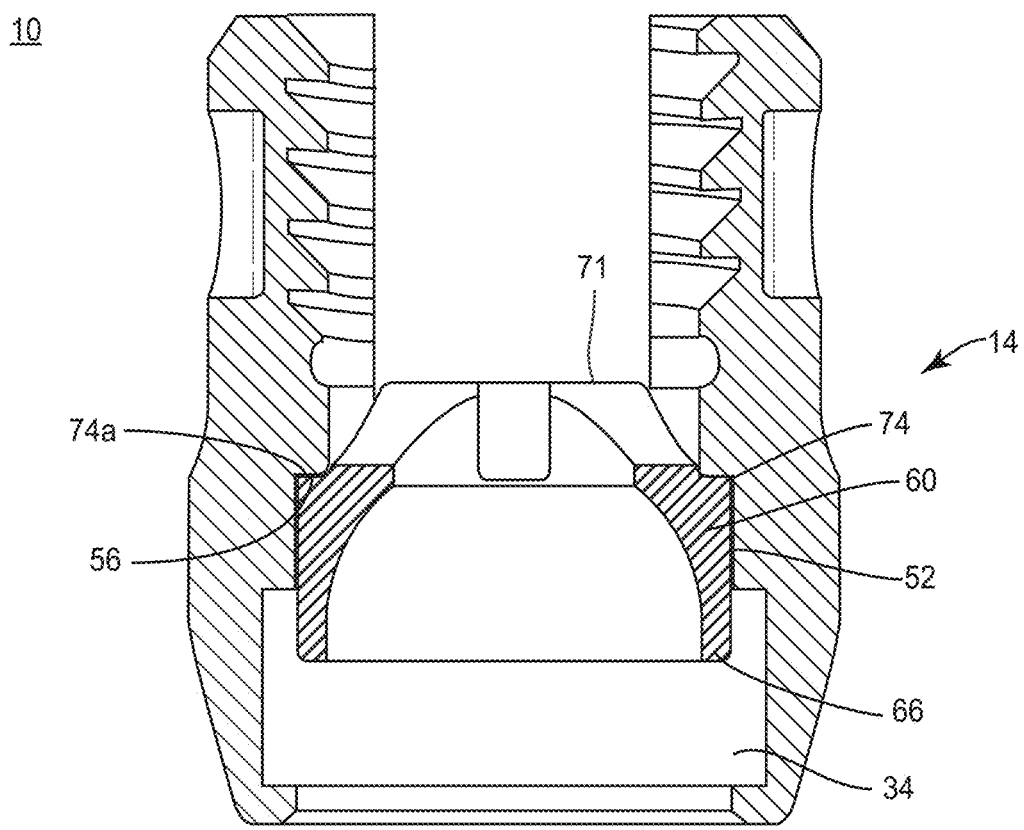
FIG. 8 is a side cross section view of the components of the system in a first position.

As an example of the translating function, FIG. 8 shows crown 60 disposed initially with receiver 14 such that portion 74a is engaged with ridge 56. Upon engagement of tool-engaging portion 79 by a surgical tool, crown 60 is rotated, for example, a 90-degree rotation, portion 74a rotates out of engagement with ridge 56 and ramp 76 rotates into engagement with ridge 56. As ridge 56 slides along ramp 76, crown 60 is translated distally, causing surface 66 to urge and/or drive spacer 80 distally along surface 30 into engagement with ring 120, as described herein. Crown 60 configured such that after it is rotated into position as described, portion 71 is oriented to receive spinal rod 200 and portion 76b is engaged with ridge 56.

Figure 5:
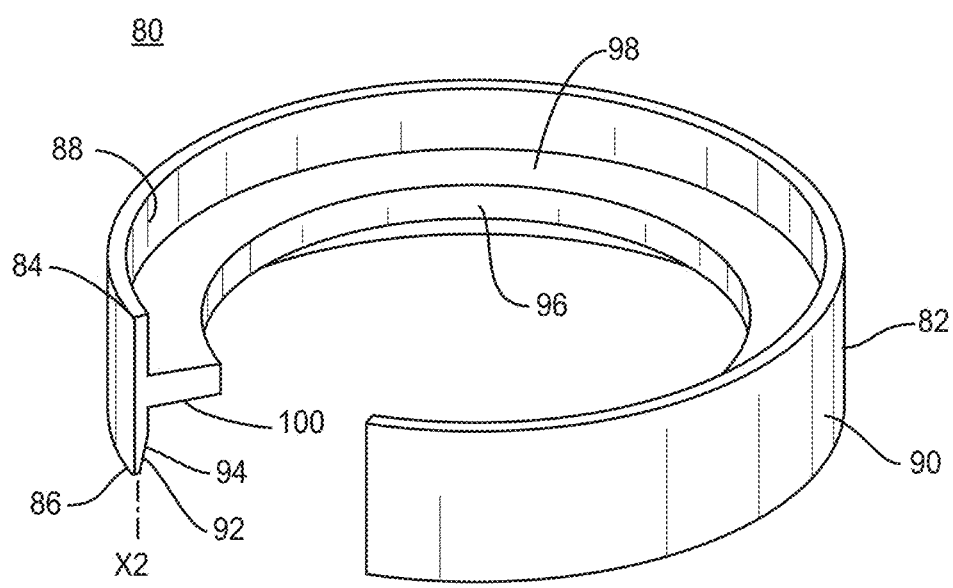
FIG. 5 is a perspective view of a third component of the system shown in FIG. 1.

Spacer 80 includes a wall 82, as shown in FIG. 5. Wall 82 extends between an end 84 and an end 86 along an axis X2. Wall 82 includes an inner surface 88 and an outer surface 90. End 86 includes a surface 92, which, in various embodiments, is disposed at least one angle, besides 90 degrees, relative to axis X2. This can define a ramp surface 94. Ramp surface 94 may be fully or partially disposed circumferentially about surface 88.

Ramp surface 94 is engageable with an outer surface of ring 120, as described herein, to dispose ring 120 (FIGS. 6, 11, et al.) in a contracted, or capture orientation, as described herein. Ramp surface 94 is inclined to, which pushed against the ring 120, cause contraction of the ring in operation.

As further shown in FIG. 5, inner surface 88 of the spacer 80 may include an inner circumferential flange 96. Flange 96 includes a first surface 98 engageable with surface 66 of crown 60 to actuate translation of spacer 60, as described herein. Surface 98 may include a planar configuration to maximize engagement with surface 66. Flange 96 includes a second surface 100 disposed on an opposite side of flange 96. Surface 100 is configured for disposal adjacent ring 120 to facilitate capture of ring 120 with receiver 14 and screw shaft 12.

Surface 90 is slidably engageable with surface 30 to facilitate axial translation of spacer 80 relative to slot 34. Spacer 80 is initially disposed with distal portion 40 such that end 86 is disposed adjacent stop surface 42 at the distalmost portion of slot 34.

In some embodiments, crown 60 is a separate element than spacer 80. In some embodiments, crown 60 is monolithically formed with spacer 80. In some embodiments, crown 60 is connected with spacer 80. In some embodiments, crown 60 is connected with spacer 80 in any of various fixation configurations, such as, for example, friction fit, pressure fit, locking protrusion/recess, locking keyway and/or adhesive. In some embodiments, spacer 80 is fixedly connected to or formed integrally with the crown 60.

In some embodiments, during assembly of receiver 14 with screw shaft 12, positioning of spacer 80 and ring 120 provides a haptic or tactile feedback to the user. For example, engagement of distal end 86 of spacer 80 with proximal surface 42 of receiver 14 provides a tactile feedback—the user feels that the spacer 80 cannot be translated further, for instance, indicating proper positioning of spacer 80 relative to receiver 14, or relative to both receiver 14 and ring 120. In some embodiments, the tactile feedback is provided by ring 120 sliding back up a head 182 of the screw shaft 12, as described herein, indicating that ring 120 is not fully translated into the capture orientation.

Figure 6:
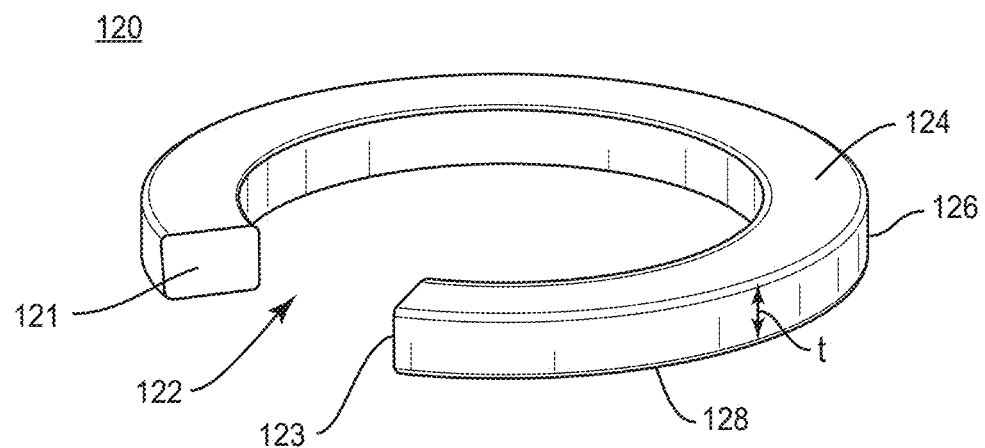
FIG. 6 is a perspective view of a fourth component of the system shown in FIG. 1.

Ring 120 extends between ends 121, 123, as shown in FIG. 6. Ring 120 includes a circumference that extends between ends 121, 123, as shown in FIG. 6. In some embodiments, the ends define a gap 122. Having gap 122 is one or various ways to provide flexibility to the ring 120. A gap 122 is not required in all embodiments, though. Ends ring 120 can overlap, for instance, and, still not being fixedly connected, still allow for relative motion. In that case, the configuration allows the overlapping ends to move with respect to each other—e.g., generally circumferentially away from each other when the ramp surface 94 is pushing inward on the ring 120. In some embodiments, one end can be sized to slidably receive the other end of the ring 120.

Ring 120 includes a surface 124, a surface 126 and a surface 128. In some embodiments, surfaces 124, 126, 128 include a planar configuration. In some embodiments, one or more of surfaces, 124, 126, 128 include any of various surface configurations, such as, for example, arcuate, offset, staggered, transverse, angular undulating, mesh, porous, semi-porous, dimpled and/or textured.

Ring 120 is disposable between an expanded orientation (FIG. 13) and a contracted, capture, orientation (FIG. 15) within slot 34 of receiver 14, as described herein. In the expanded orientation, ring 120 is disposed at the distalmost portion such that surface 128 is engaged with stop surface 42 of slot 34. In the capture orientation, surface 124 is engaged with surface 100, surface 126 is engaged with ramp surface 94 and surface 128 is engaged with edge surface 42.

Figure 7:
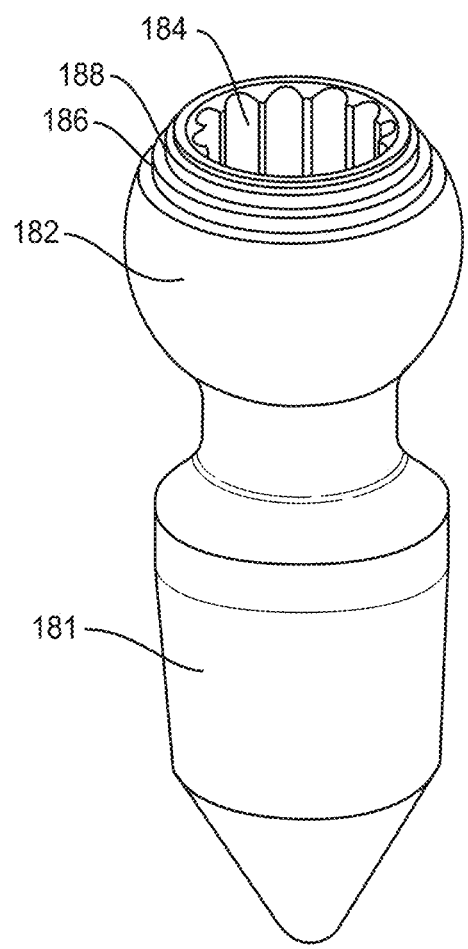
FIG. 7 is a perspective view of a fifth component of the system shown in FIG. 1.

Screw shaft 12 includes shaft 181 and head 182, as shown in FIG. 7. Shaft 181 is configured to penetrate tissue, such as, for example, vertebral tissue. In some embodiments, shaft 181 includes an outer surface having an external thread form. In some embodiments, the external thread form may include a single thread turn or a plurality of discrete threads. Head 182 includes a tool engaging portion 184 configured to engage a surgical tool or instrument, as described herein. In some embodiments, portion 184 includes a hexagonal cross-section. In some embodiments, portion 184 may have alternative cross-sections, such as, for example, rectangular, polygonal, hexalobe, oval, or irregular. Head 182 includes a surface 186 that defines a plurality of ridges 188 to improve purchase of head 182 with crown 60.

In some embodiments, receiver 14 may be disposed with head 182 in any of various fixation configurations, such as, for example, friction fit, pressure fit, locking protrusion/recess, locking keyway and/or adhesive. In some embodiments, receiver 14 is configured for rotation relative to head 182 for multi-axial movement. In some embodiments, receiver 14 is configured for rotation in range of 360 degrees relative to head 182 to facilitate positioning of shaft 181 with tissue. In some embodiments, receiver 14 is configured for selective rotation in range of 360 degrees relative to and about head 182 such that shaft 181 is selectively aligned for rotation in a plane relative to receiver 14. In some embodiments, receiver 14 may be disposed with head 182 in a uni-axial configuration or a sagittally adjustable configuration.

In some embodiments, screw shaft assembly 12 is manually engageable with head assembly 13 in a non-instrumented assembly process, as described herein. In some embodiments, manual engagement and/or non-instrumented assembly of head assembly 13 and screw shaft assembly 12 includes coupling without use of separate and/or independent instrumentation engaged with screw shaft assembly 12 components to effect assembly. In some embodiments, manual engagement and/or non-instrumented assembly includes a practitioner, surgeon and/or medical staff grasping head assembly 13 and screw shaft assembly 12 and forcibly assembling the components. In some embodiments, manual engagement and/or non-instrumented assembly includes a practitioner, surgeon and/or medical staff grasping head assembly 13 and screw shaft assembly 12 and forcibly snap fitting the components together, as described herein. In some embodiments, manual engagement and/or non-instrumented assembly includes a practitioner, surgeon and/or medical staff grasping head assembly 13 and screw shaft assembly 12 and forcibly pop fitting the components together and/or pop fitting head assembly 13 onto screw shaft assembly 12, as described herein. In some embodiments, a force in a range of 2-50 N is required to manually engage head assembly 13 and screw shaft assembly 12 and forcibly assemble the components. For example, a force in a range of 2-50 N is required to snap fit and/or pop fit assemble head assembly 13 and screw shaft assembly 12. In some embodiments, a force in a range of 5-10 N is required to manually engage head assembly 13 and screw shaft assembly 12 and forcibly assemble the components. For example, a force in a range of 5-10 N is required to snap fit and/or pop fit assemble head assembly 13 and screw shaft assembly 12. In some embodiments, this configuration provides manually engageable components that are assembled without instrumentation, and subsequent to assembly, the assembled components have a selected pull-out strength and/or can be pulled apart, removed and/or separated with a minimum required force.

In some embodiments, spinal implant system 10 comprises a spinal implant kit, as described herein, which includes a plurality of screw shaft assemblies 12 and/or head assemblies 13. Screw shaft assembly 12 and/or head assembly is configured for selection such that the components of bone fastener 180 are interchangeable.

In assembly, operation and use, spinal implant system 10, similar to the systems and methods described herein, includes a screw shaft assembly 12 for connection with a head assembly 13, and is employed with a surgical procedure for treatment of a spinal disorder affecting a section of a spine of a patient, as discussed herein. Spinal implant system 10 is employed with a surgical procedure for treatment of a condition or injury of an affected section of the spine.

In some embodiments, a screw shaft assembly 12 is selected from a kit of a plurality of screw shaft assemblies 12 for interchangeable connection with head assembly 13 to comprise a bone fastener 180 having a selected movement, similar to those described herein. In some embodiments, the kit of screw shaft assemblies 12 includes a variety of screw shaft assemblies having different movement configurations when assembled with an interchangeable head assembly 13, such as, for example, multi-axial movement, sagittal angulation movement, fixed axis movement, mono-axial movement and/or uni-planar movement.

Figure 9:
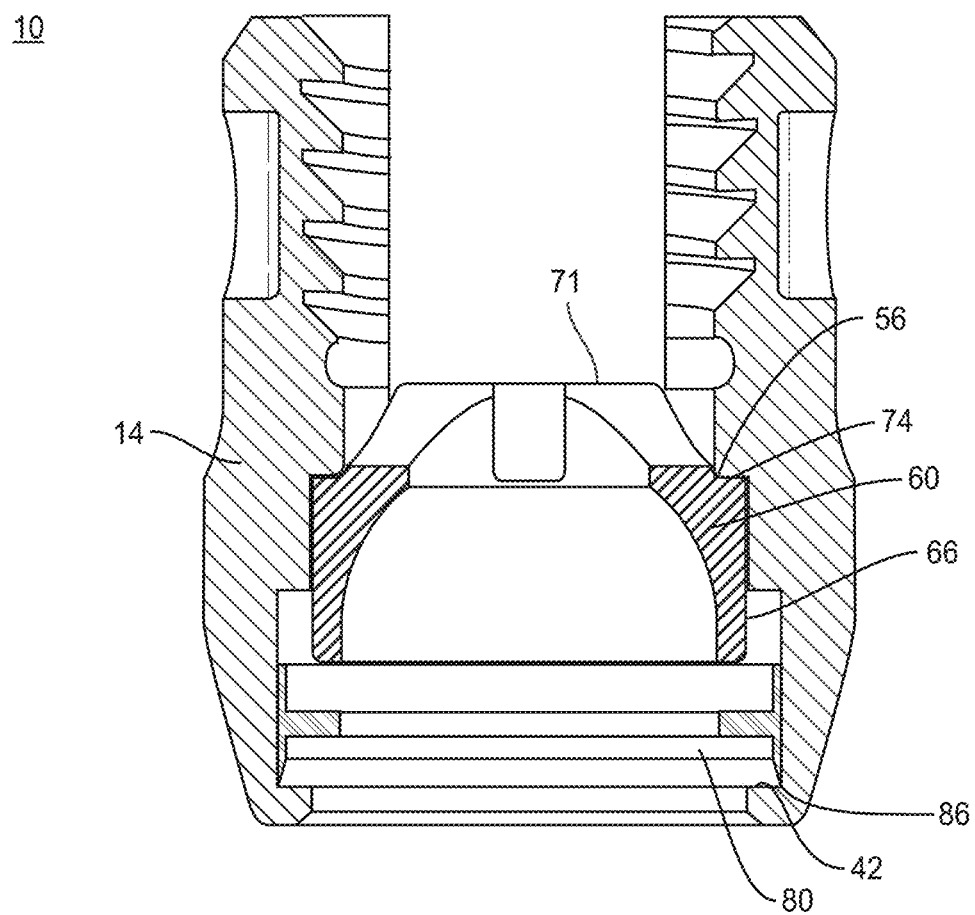
FIG. 9 is a side cross section view of the components of the system in a second position
Figure 10:
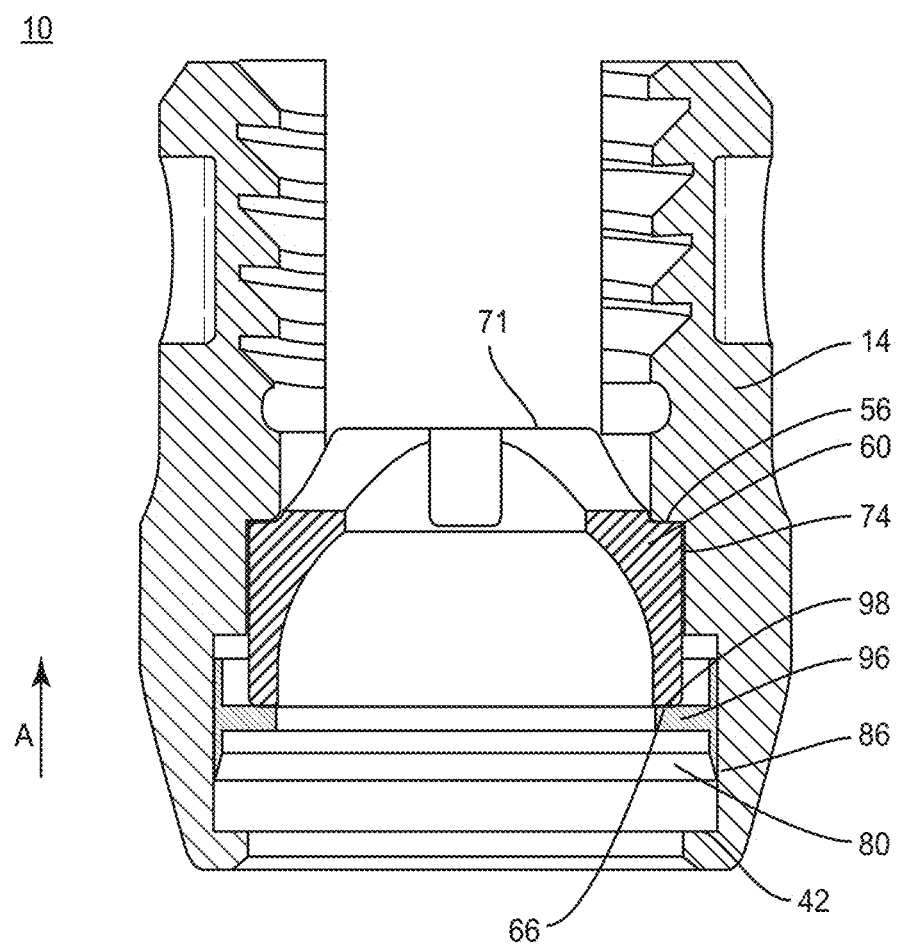
FIG. 10 is a side cross section view of the components of the system in a third position.

In some embodiments, head assembly 13 includes receiver 14 assembled with crown 60, spacer 80 and ring 120, as shown in FIGS. 8-15. Crown 60 is initially disposed with receiver 14 such that portion 71 of crown 60 is not oriented to receive spinal rod 200, wherein the rod-receiving area for receiving the rod is aligned to pass through the arms 16, 18 of the receiver 14, instead of between the arms, as shown in FIG. 8. In this position, portion 74a of ridge 74 is slidably engaged with ridge 56. Spacer 80 is assembled with receiver 14, as shown in FIGS. 9 and 10. Spacer 80 is initially disposed with distal portion 40 such that end 86 is disposed adjacent stop surface 42 at the distalmost portion of slot 34. Spacer 80 is translated, in a direction shown by arrow A in FIG. 10, such that surface 98 of flange 96 is engaged with surface 66 of crown 60.

Figure 11:
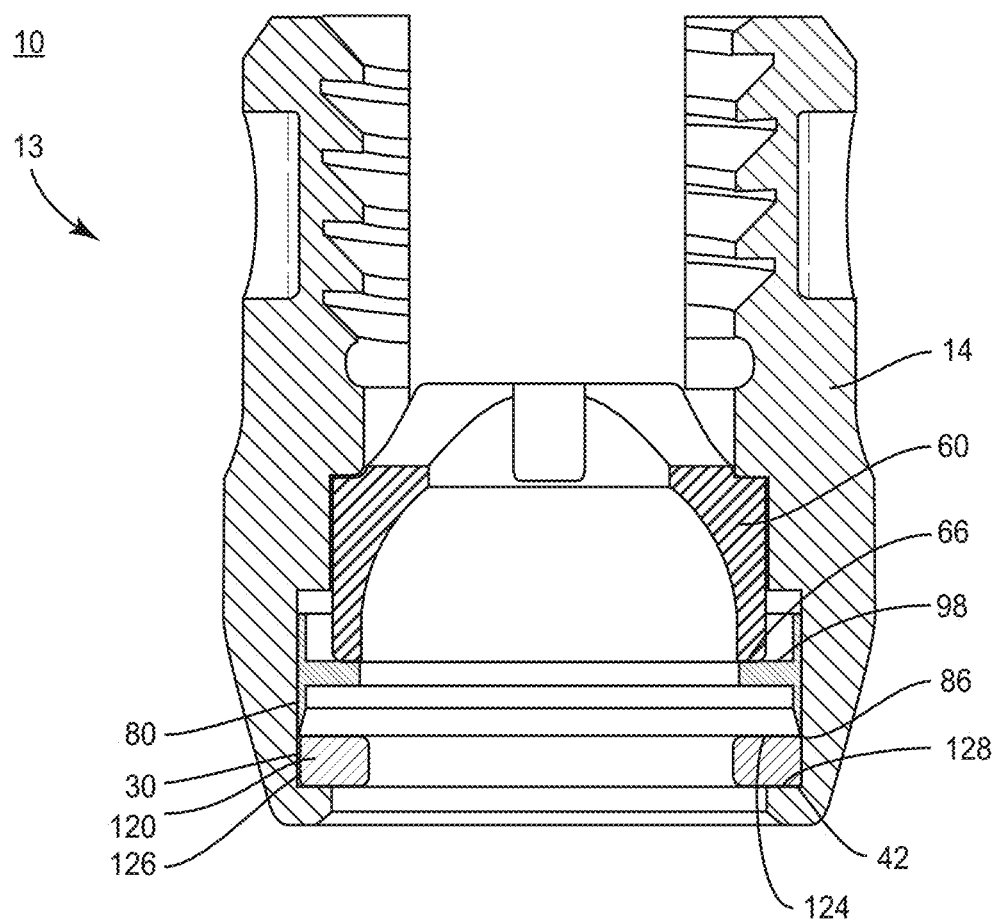
FIG. 11 is a side cross section view of the components of the system in a fourth position.
Figure 12:
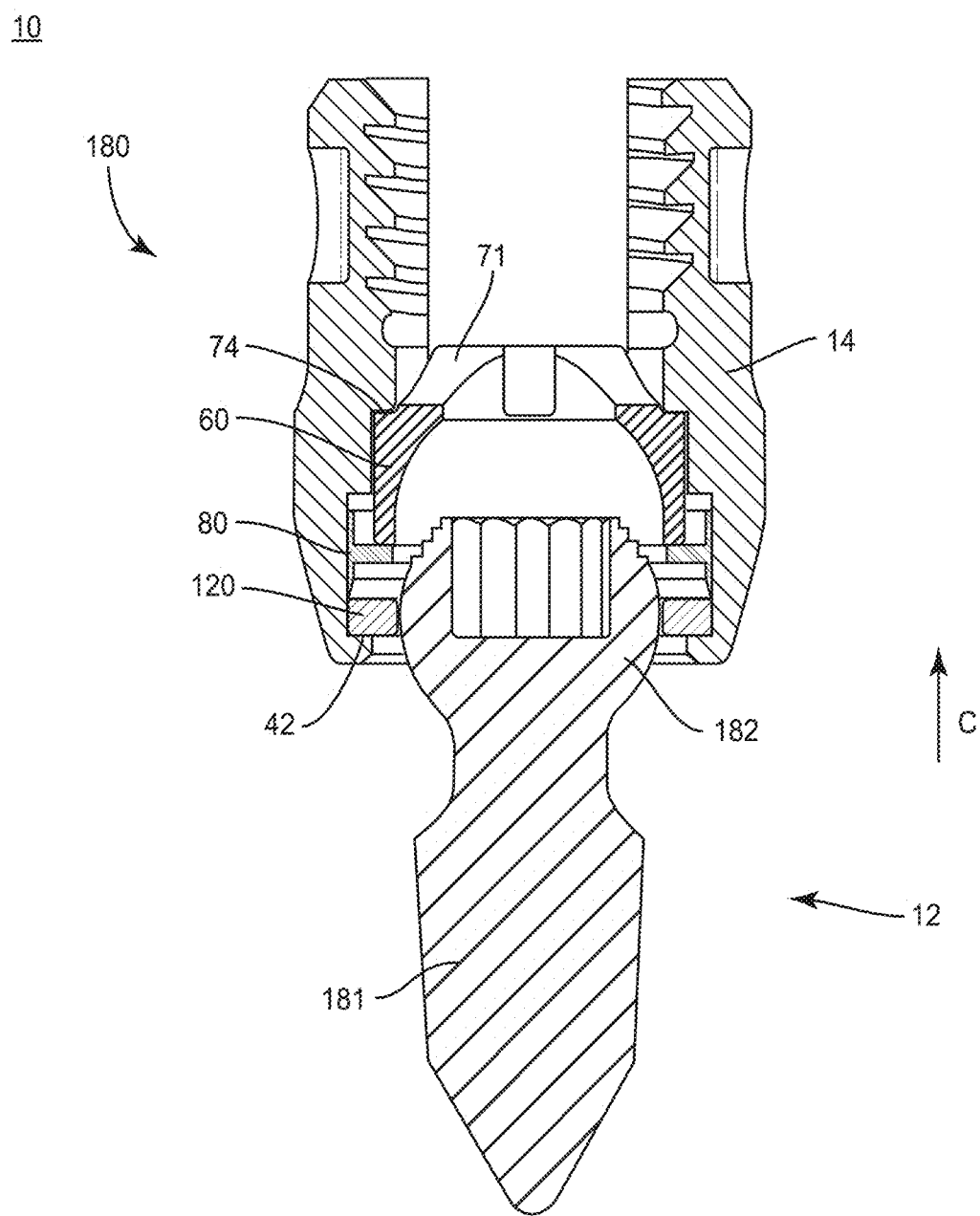
FIG. 12 is a side cross section view of the components of the system in a fifth position.

Ring 120 is assembled with receiver 14, as shown in FIG. 11. Ring 120 is initially disposed with receiver 14 in an expanded orientation such that surface 126 engages surface 30. Ring 120 is disposed with distal portion 40 such that surface 128 is disposed adjacent stop surface 42 at the distalmost portion of slot 34. End 86 of spacer 80 is disposed adjacent surface 124 of ring 120.

Figure 13:
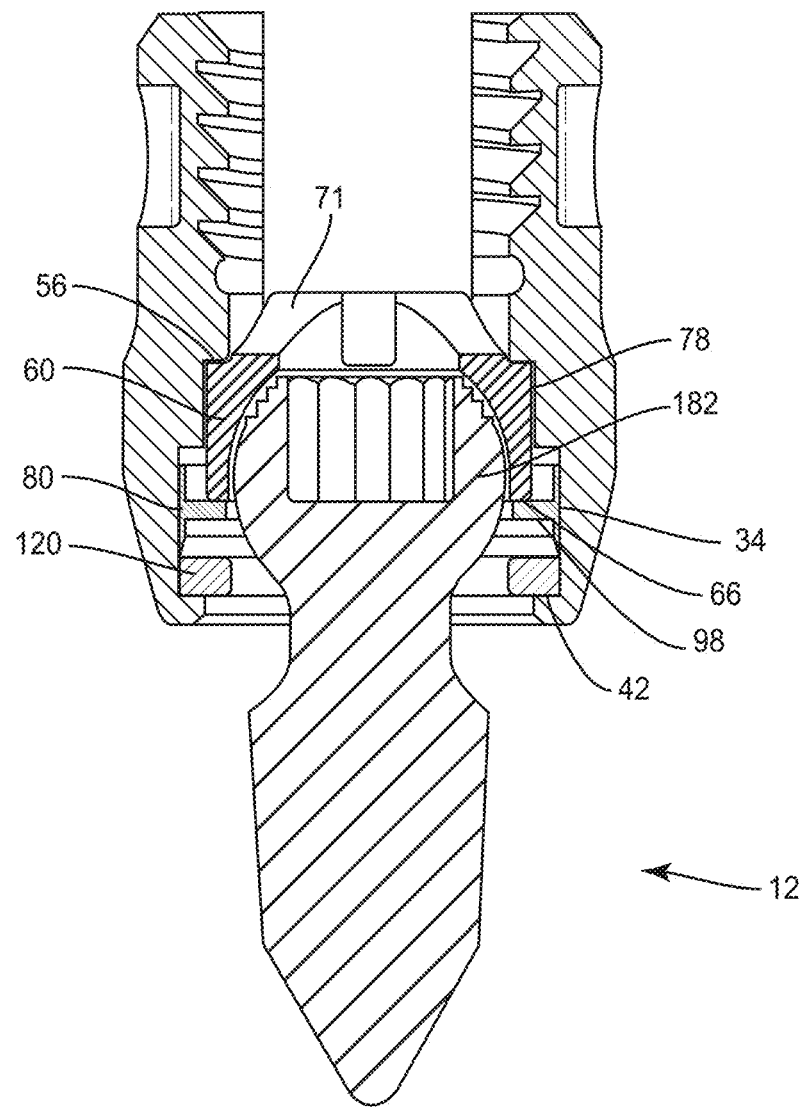
FIG. 13 is a side cross section view of the components of the system in a sixth position.

Screw shaft 12 is manually engageable, as described herein, with head assembly 13, as shown in FIGS. 12-15. Head assembly 13 is assembled with screw shaft 12 by translating screw shaft 12, in a direction shown by arrow C in FIG. 12. Head 182 translates through ring 120. Ring 120 in its expanded orientation provides for a substantially frictionless translation of head 182 therethrough. Head 182 translates into engagement with surface 78 of crown 60, as shown in FIG. 13.

A surgical instrument is engaged with portion 79 of crown 60 to actuate rotation of crown 60, as shown by arrow D in FIG. 14. As crown 60 rotates, portion 74a of ridge 74 rotates out of engagement with ridge 56 and ramp 76 rotates into engagement with ridge 56. As ridge 56 slides along ramp 76, crown 60 is translated, in the direction shown by arrow E in FIG. 14. Crown 60 is rotated such that portion 76a is engaged with ridge 56. In some embodiments, crown 60 can be rotated in the opposite direction 90 degrees to facilitate disassembly of the components.

Translation of ridge 56 along ramp 76 and into engagement with portion 76a causes surface 66 to urge and/or drive spacer 80, in a direction shown by arrow F in FIG. 15, along surface 30. As spacer 80 translates, end 86 of spacer 80 engages surface 126 of ring 120. End 86 compresses ring 120, in a direction shown by arrows G in FIG. 15, and slides between surface 126 and surface 30. Surface 126 translates along ramp surface 94 causing ring 120 to further contract relative to head 182. Ramp surface 94 is disposed in an interference orientation between surface 30 and surface 126 of ring 120 to resist and/or prevent expansion of ring 120. Contraction of ring 120 captures head 182 and locks head assembly 13 with screw shaft 12. If crown 60 is not rotated the complete 90 degrees spacer 80 is not translated into engagement with stop surface 42, a tactile feedback will indicate improper positioning to the user, as described herein.

Once crown 60 is rotated 90 degrees, as described herein, portion 71 to be oriented to receive spinal rod 200. Spinal rod 200 is disposed with receiver 14 and portion 71 and setscrew 202 is engaged with thread form 24 to fix spinal rod 200 with receiver 14. Fixation of spinal rod 200 with receiver 14 via setscrew 202 releasably locks head assembly 13 with screw shaft 12. For example, head assembly can be detached from screw shaft 12 by use of a tool if bone fastener 180 is damaged once installed or crown 60 becomes deformed.

In use, for treatment of a spinal disorder, bone fastener 180 including assembled screw shaft 12 and head assembly 13 can be threaded and engaged with tissue. In some embodiments, bone fastener 180 is disposed adjacent vertebrae at a surgical site and is manipulated to drive, torque, insert or otherwise connect shaft 181 with vertebrae in connection with a surgical procedure, as described herein.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In some embodiments, spinal implant system 10 can include one or a plurality of bone fasteners 180 such as those described herein and/or fixation elements, which may be employed with a single vertebral level or a plurality of vertebral levels. In some embodiments, bone fasteners 180 may be engaged with vertebrae in various orientations, such as, for example, series, parallel, offset, staggered and/or alternate vertebral levels. In some embodiments, bone fasteners 180 may be employed with wedges, anchors, buttons, clips, snaps, friction fittings, compressive fittings, expanding rivets, staples, nails, adhesives, posts, connectors, fixation plates and/or post.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A bone fastener comprising:
a receiver defining an implant cavity and including an inner surface defining a slot;
a band disposable within the slot;
a spacer disposable within the slot;
a crown being rotatable relative to the receiver to translate the spacer distally relative to the inner surface such that the spacer orients the band in a capture orientation; and
a screw shaft connectable with the receiver by the band and configured to penetrate tissue,
wherein the spacer is disposable in a distalmost position with the slot and engageable with the band in the capture orientation to permanently lock the receiver with the shaft.

2. A bone fastener as recited in claim 1, wherein the spacer is engageable with the band to dispose the band in a contracted, capture orientation to fix the receiver with the shaft.

3. A bone fastener as recited in claim 1, wherein the spacer is disposable in the distalmost position to provide tactile feedback.

4. A bone fastener as recited in claim 1, wherein the band is disposable between an expanded orientation and a contracted, capture orientation.

5. A bone fastener as recited in claim 1, wherein the band includes a circumferential ring defining a gap.

6. A bone fastener as recited in claim 1, wherein the spacer is fixedly connected to or formed integrally with the crown.

7. A bone fastener as recited in claim 1, wherein the spacer includes an outer surface being slidably engageable with the inner surface to facilitate axial translation of the spacer relative to the slot.

8. A bone fastener as recited in claim 1, wherein the spacer includes an inner circumferential flange engageable with a distal end surface of the crown.

9. A bone fastener as recited in claim 1, wherein the spacer includes a ramp surface engageable with the band.

10. A bone fastener as recited in claim 1, wherein the spacer includes an inner circumferential ramp surface engageable with an outer surface of the band to dispose the band in a contracted, capture orientation.

11. A bone fastener as recited in claim 1, wherein the rotatable crown includes a cam surface engageable with the receiver to axially translate the crown relative to the receiver.

12. A bone fastener as recited in claim 11, wherein the cam surface includes a circumferential ridge disposed about at least a portion of the crown.

13. A bone fastener as recited in claim 1, wherein the shaft is manually engageable with the receiver for non-instrumented assembly.

14. A bone fastener comprising:
a receiver defining an implant cavity and including an inner surface defining a slot;
a band disposable within the slot;
a spacer disposable within the slot, the spacer including a ramp surface engageable with the band;
a crown being rotatable relative to the receiver to translate the spacer distally relative to the inner surface such that the spacer orients the band in a capture orientation; and
a screw shaft connectable with the receiver by the band and configured to penetrate tissue.

15. A bone fastener as recited in claim 14, wherein the ramp surface is engageable with an outer surface of the band to dispose the band in a contracted, capture orientation.

16. A bone fastener as recited in claim 14, wherein the spacer is engageable with the band to dispose the band in a contracted, capture orientation to fix the receiver with the shaft.

17. A bone fastener as recited in claim 14, wherein the band is disposable between an expanded orientation and a contracted, capture orientation.

18. A bone fastener comprising:
a receiver defining an implant cavity and including an inner surface defining a slot;
a band disposable within the slot;
a spacer disposable within the slot;
a crown being rotatable relative to the receiver to translate the spacer distally relative to the inner surface such that the spacer orients the band in a capture orientation, the crown including a cam surface engageable with the receiver to axially translate the crown relative to the receiver; and
a screw shaft connectable with the receiver by the band and configured to penetrate tissue.

19. A bone fastener as recited in claim 18, wherein the cam surface includes a circumferential ridge disposed about at least a portion of the crown.

20. A bone fastener as recited in claim 18, wherein the spacer is engageable with the band to dispose the band in a contracted, capture orientation to fix the receiver with the shaft.

21. A bone fastener as recited in claim 18, wherein the band is disposable between an expanded orientation and a contracted, capture orientation.

* * * * *